United States Patent [19]

Sams

[11] Patent Number: 5,304,152

[45] Date of Patent: Apr. 19, 1994

[54] DISPENSING DEVICE

[76] Inventor: Bernard Sams, 103 Friern Barnet Road, London, United Kingdom, N11 3EU

[21] Appl. No.: 773,610

[22] PCT Filed: Mar. 28, 1991

[86] PCT No.: PCT/GB91/00489

§ 371 Date: Nov. 27, 1991

§ 102(e) Date: Nov. 27, 1991

[87] PCT Pub. No.: WO91/14467

PCT Pub. Date: Oct. 3, 1991

[30] Foreign Application Priority Data

Mar. 29, 1990 [GB] United Kingdom ................ 9007113

[51] Int. Cl.$^5$ ............................................. A61M 5/00
[52] U.S. Cl. .................................. 604/207; 604/208; 604/211; 604/218
[58] Field of Search ............... 604/187, 218, 207–211, 604/224, 232, 71, 72

[56] References Cited

U.S. PATENT DOCUMENTS

| 4,498,904 | 2/1985 | Turner et al. | 604/211 |
| 4,561,856 | 12/1985 | Cochran | 604/143 |
| 4,592,745 | 6/1986 | Rex et al. | 604/211 |
| 4,883,472 | 11/1989 | Michel | 604/208 |
| 4,936,833 | 6/1990 | Sams | 604/232 |
| 4,968,299 | 11/1990 | Ahlstrand | 604/90 |
| 4,973,318 | 11/1990 | Holm et al. | 604/208 |
| 5,017,190 | 5/1991 | Simon et al. | 604/207 |
| 5,042,977 | 8/1991 | Bechtold et al. | 604/134 |
| 5,104,380 | 4/1992 | Holman et al. | 604/117 |
| 5,112,317 | 5/1992 | Michel | 604/208 |

Primary Examiner—C. Fred Rosenbaum
Assistant Examiner—Mark O. Polutta
Attorney, Agent, or Firm—Varnum, Riddering, Schmidt & Howlett

[57] ABSTRACT

A dispensing device has a shell (11) which may be connected to a container (14) for a fluid to be dispensed, such as an injectable pharmaceutical compound. The device has a fixed first threaded member (21) and a second threaded member (22) surrounding the first member, the first and second members each having equi-spaced threaded segments (27 and 29) with non-threaded segments (28) therebetween whereby the second member will be wound axially when rotated about the first member but may be positioned for axial sliding movement with respect to the first member. A plunger (23) is slidably mounted within the first member (21) and has a portion (33) engageable with the threads of the second member. A dose setting sleeve (53) surrounds the second member and has threads (54) engaged with the device shell, the sleeve being coupled to the second member for rotation therewith. A dose is set by winding the second member (22) away from a fixed stop (25) until the sleeve (53) indicates the required does amount, whereafter the second member (22) is slid axially back to the fixed stop (25), the plunger (23) being thrust forwardly thereby to expel fluid from the container.

14 Claims, 4 Drawing Sheets

DISPENSING DEVICE

BACKGROUND OF THE INVENTION

1. Field of the Invention

The present invention relates to a dispensing device which is arranged to dispense an accurate and measured dose of a fluid. Typically such a fluid may be one which is itself or which contains a therapeutically or otherwise active compound or composition, such as insulin.

2. Description of the Related Art

European Patent Specification No. 0,037,696 A discloses a dispensing device suitable for use in dispensing a predetermined quantity of material from a container comprising a tubular body member having an outlet at one end, and a plunger slidably movable in said body member towards said outlet. The dispensing device comprises an elongate body having a chamber for receiving a container with its outlet held in a first end portion of the elongate body, and a first drive member mounted in said body for use in driving said plunger. In the disclosed device said first drive member is slidably mounted for driving engagement via a unidirectional drive transmission with a second drive member having a free end drivingly engagable with said plunger of the container. In that manner said second drive member and said plunger can be driven by the first drive member via said unidirectional drive transmission means only in a direction towards the container outlet and the first end portion of the elongate body whilst permitting return movement of the first drive member. Preferably, the unidirectional drive transmission comprises a ratchet means.

For setting the dose to be dispensed the adjust knob is turned to align a pin with one of a series of channels of varying length (dependent on the size of dose required) in the push button (or vice versa). The length of the channel dictates the movement forward of the plunger and the multiple of doses is decided by how many channels one can safely have around the circumference consistent with side walls to each channel and the size of the readout on the circumference.

A usable diameter gives eight variable doses. One could increase the diameter to give more channels and more variations of dose. However, the device would become more and more unwieldy as the number of channels is increased.

Another serious fault with this device is that it is easy to pump the push button so that the plunger moves forward without the pin ever reaching the bottom of its channel. This is unsafe.

European Patent Specification No. 0,295,075 A relates to a device for dispensing a fluid from a container by means of the axial movement of a piston within the container under the influence of a plunger moved by the device. The device is adapted to receive the container at its forward end and to move the plunger axially forward towards the container so as to dispense a selected amount of fluid from the container upon each actuation of the device. The device comprises a drive mechanism adapted to be reciprocated axially of the device and to be positively engaged with the plunger for the forward stroke of the drive mechanism so as to prevent relative movement between the plunger and the drive mechanism and to move the plunger forward. The drive mechanism requires a positive action to disengage it from the plunger so as to permit relative movement between the plunger and drive mechanism for at least rearward movement of the drive mechanism. Also, the forward travel of the drive mechanism is limited by a fixed stop mechanism and the extent of the forward stroke of the drive mechanism is individually selectable for each actuation of the device by withdrawing the drive mechanism or a part operatively associated therewith a selected distance from the said fixed stop.

The device of EP-0,295,075 A is designed to give a maximum of 36 units of insulin. For dose setting opposed jaws are pulled back in a slot by rotating a screw, the length of slot being determined by the length of the movement forward of the plunger at maximum dose. A larger dose means a longer slot and a corresponding lengthening of the device. In addition, to wind back the screw for an additional dose means a lengthening of the screw in the main body, thereby adding another additional dose length to the device. Also, in line with the jaws and screw is the readout which needs an additional dose length and a corresponding increase in body length. Thus, there is a ratio of 3:1 between body length and plunger length, which means that each time the dose is increased there is an additional three millimeters of body length for every millimeter of plunger length necessary to give the higher dose setting.

In prior art dispensing devices, such as those outlined above, the usual dispensing increment is 2 units, but the amount dispensed for a given standard length of device is limited. Thus, in the case of a patient wishing to use a relatively large dose it may be necessary to use the device twice or even more times, each time to dispense a smaller dose.

SUMMARY OF THE INVENTION

This invention aims at overcoming the above-mentioned problems of the described prior art devices, and in particular at providing a dispensing device which can dispense relatively large doses and yet which has a body length to plunger length ratio of about 1:1.

Accordingly, in one aspect the present invention provides a device for dispensing a controlled amount of fluid from a container, which device comprises a device for dispensing controlled doses of fluid from a container having a piston movable axially in increments thereby to dispense doses of fluid from an outlet of the container, which device comprises means to connect the device to a container, a plunger engageable with the container piston, and a dose setting and dispensing arrangement having first and second threaded members, the first member being fixed in relation to the device and the second member being mounted for rotation about the first member and having threads engageable with those of the first member, the plunger being slidably mounted within the first member and having a portion engageable with the threads of the second member, and the second member being rotatable to any one of a plurality of settings where its threads are engaged with said portion of the plunger but free of the first member whereby the second member and plunger may slide axially relative to the first member, movement of the second member in a direction towards the container connection means being limited by a fixed stop, the device further comprising dosage indicator means connected to the second member and arranged to indicate an ascending series of measured doses as the second member is rotated to move along the threads of the first member away from said fixed stop whilst the plunger remains stationary, and for each indicated dose the second member is disposed in one of its said settings relative to the first member where axial movement of the second member is permitted, the second member during such movement driving the plunger to act on the piston of a connected container and the dose expelled thereby being controlled by the axial distance of travel of the second member to the fixed stop from the position to which said member has been turned to indicate a desired dose.

The device of the invention is generally intended to be used as a hand portable device and preferably as the dose dispensing portion of a syringe. Typically, such a syringe is of the kind used by diabetics to dispense insulin on a regular daily basis, but of course may be used by other patients and for other situations.

For use as a syringe the device is connected to a container provided with a reservoir of fluid which either itself may be an active material or may be the carrier for and contain an active material. The container at its outlet end typically may include connection means for a hypodermic needle and at its opposite end may include means for connection to the connecting means of the device. The latter means may comprise a threaded portion of a bayonet fixing arrangement. Known containers are generally tubular, and adapted to receive a fluid cartridge having a piston moveable therein.

The device preferably includes a cylindrical shell in which is fixed the first member, and within which the second member may rotate about the first member. The first member may be threaded externally with a plurality (and preferably four) of equi-spaced threaded arcuate sectors separated by a like plurality of non-threaded sectors. In this case, the second member should comprise a hollow cylinder threaded internally with threaded and non-threaded sectors arranged in essentially the same configuration as that of the first member. The second member will thus be free of the first member and free to move axially at some rotational dispositions, but at others will be engaged with the first member and so moved axially on being turned. To allow re-engagement of the respective threads when the second member has been moved axially to the fixed stop, the threads are preferably of multi-start form, advantageously of the same number of starts as threaded sectors. It will (of course) be understood that other numbers of threaded and non-threaded sectors besides four may be used as desired, and that the invention is not limited to the described four.

In the above arrangement the second member may be wound backwards and forwards on the first member, but may be disposed relative to the first member to have their respective threads disengaged, whereby the second member is slidable axially of the first member and device shell.

The plunger is preferably slidably received within a slot in the first member, said portion engageable with the threads of the second member projecting through a non-threaded sector of the first member.

Said portion of the plunger may comprise one of an arcuate threaded portion of the same thread form as that of the second member. Alternatively, said portion may comprise a toothed wheel rotatably mounted on the plunger and having teeth formed to be engageable with the threads of the second member. Axial sliding movement of the second member will thus also slide the plunger by virtue of the interengagement of said plunger portion with the second member threads.

Where said portion comprises a simple thread, the plunger will move together with the second member, but in the case of the said portion comprising a toothed wheel, a rack may be formed on a fixed part of the device and with which the wheel meshes, so that the wheel rotates on axial movement of the plunger; then the plunger will move through one half of the axial sliding movement of the second member as the wheel rolls along the rack.

Dose setting and dispensing is performed by initially winding the second member away from the fixed stop, the plunger remaining stationary, until the second member is spaced from that stop by some predetermined instance. The second member is set to permit axial sliding movement and is then slid back to contact the fixed stop. During this, the plunger is thrust forward, so driving the cartridge piston and dispensing the required, set dose.

In order to permit the selection of a required dose, and so the distance from the fixed stop to which the second member is wound, the second member is linked to a dosage indicator means. Such means may comprise a sleeve carrying an ascending series of dose numbers, the sleeve being arranged to be threaded along the device shell as the second member is rotated, whereby the more the second member is threaded away from the fixed stop, the higher will the indicator dose number.

For each dose displayed by the indicator means, the second member is advantageously in one of its settings where its threads are disengaged from those of the first member. At each displayed dose, axial movement of the second member and linked plunger is permitted, to dispense the displayed dose by the plunger acting on the cartridge piston.

Said sleeve preferably has external threads engaged with internal threads on the device shell, said threads being of the same pitch as those of the first and second members so that the sleeve and second member move the same axial distance on each rotation thereof. A rotatable but axially fixed dose control knob may be provided linked to said sleeve and the second member by a splined connection.

In the device of the invention, the indicator means is preferably linked to the second member through a clutch arrangement. This conveniently is a form of dog-clutch having a like number of dogs and recesses as threaded sectors on the second member. After dispensing a set dose, the indicator sleeve may be wound back to zero, the dog clutch picking up the second member as the sleeve returns to its zero position, ready to be wound out together with the second member to set a new dose.

Preferably lock means are provided to restrain rotation of the second member in a sense which moves the second member away from the fixed stop when the plunger projects from the second member by more than a pre-determined amount. Thus, should a user try to set a dose greater than that remaining in a cartridge connected to the device, the second member will be locked at the maximum possible dose from the connected cartridge, the indicator means indicating (at lock) the amount of that dose.

This invention extends to the combination of a dose dispensing device as described above in combination with a body defining a chamber for receiving a container for fluid, support means for a dispensing needle communicating with an outlet from the container. Such a combination may take the form of a medical syringe, typically for dispensing medications such as insulin.

BRIEF DESCRIPTION OF THE DRAWINGS

By way of example only, specific embodiments of the device of the invention will now be described by way of example only and with reference to the accompanying drawings, in which.

DETAILED DESCRIPTION OF THE PREFERRED EMBODIMENTS

Figure 1:
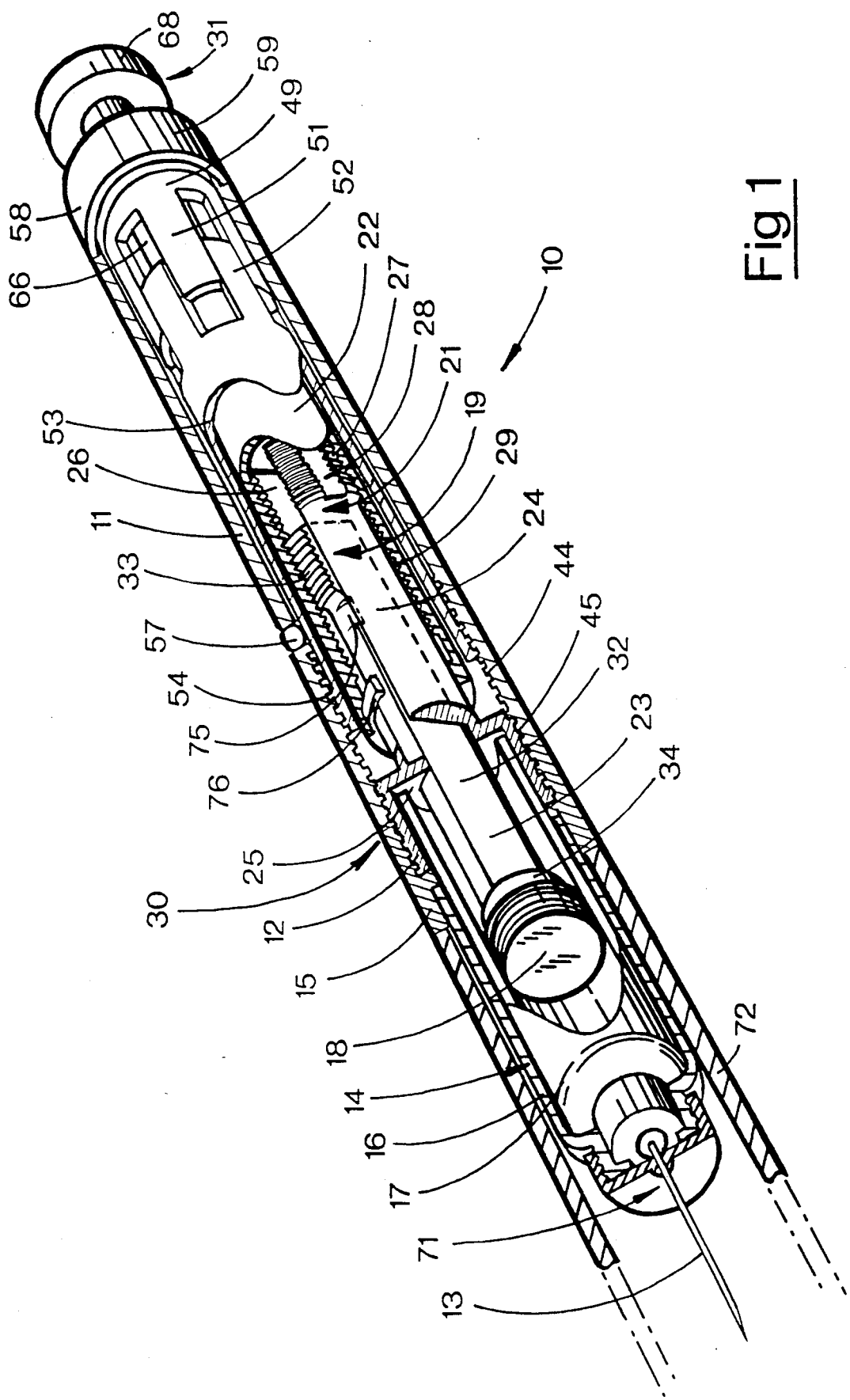
FIG. 1 is a cut-away perspective view of a dispensing device according to the invention.

Referring to FIG. 1, the device 10 comprises a main body shell 11 which includes at its front end a threaded connector 12 by means of which the shell may be connected to a container 14 having a connector portion 15, to hold the device 10 and the container 14 in a fixed relationship. The container 14 is of known type comprising an outer protective plastics housing 16 in which is received an inner glass cartridge 17 having a captive piston 18 and containing the fluid to be dispensed (not shown) out of a hypodermic needle 13.

Within the body shell 11 there is a dose setting and dispensing arrangement 19 comprising first and second threaded members 21 and 22, and a plunger 23. First member 21 comprises side elements 24 held by ring 25 in a fixed relationship to form a slot 26 in which is slidable the plunger 23. The ring 25 is formed integrally with connector 12, which serves to hold member 21 in a fixed relationship to the shell 11.

Each element 24 comprises upper and lower threaded segments 27 separated by a non-threaded channel 28 so that member 21 overall comprises four threaded segments 27, each separated by one of four plain non-threaded segments as provided by channels 28 and slot 26.

First member 21 carries on its threaded segments 27 the second member 22 which is a hollow cylindrical collar having four threaded inner segments 29 the configuration of which matches that of the threaded segments 27. Thus, the member 22 may be wound e.g. towards the rear end 31 of the device 10, upon rotation of member 22, by the interengagement of the threaded segments 27 and 29, but that member 22 also may slide e.g. towards the front end 30 of the device 10, when opposed threaded segments 29 are in register with channels 28. In the arrangement shown, each 90° of rotation of member 22 initially moves member 22 axially by the interaction of its threaded segments 29 with segments 27 of member 21, and then segments 29 come into alignment with the non-threaded portions of member 21, allowing member 22 to be pushed forwards or backwards with respect to member 21. The depth of the channels 28 thus need be only sufficiently deep to give clearance for the threaded segments 29 of member 22.

It would be possible to configure the members 21 and 22 with different numbers of threaded segments to permit sliding movement at positions other than at 90° spacings, and any suitable number of positions may be employed as desired.

Plunger 23 is elongate, as shown, and includes flat sides 32 which enable it freely to slide axially in slot 26. The plunger 23 has an upper threaded segment 33 which together with segments 27 form an arcuate thread on which member 22 is carried. However, when the device is in the dose dispensing mode where segments 29 are free of segments 27, segment 33 remains meshed with a segment 29 of the member 22, whereby forward movement of member 22 towards the fixed stop ring 25 carries the plunger 23 forward, to ensure that the correct measured dose is dispensed. The forward end 34 of the plunger 23 acts on the piston 18, to move the piston 18 within cartridge 17 and dispense the required dose.

When the member 22 is pushed forward to hit the stop ring 25, the member 22 will be in one of four rotational positions spaced by 90° (or some other number for different configurations). In order to pick up the threads on member 21 at each of the four possible positions of member 22 at the stop ring, the thread helix should have a like number of starts as possible positions, and the threaded segment 33 of plunger 23 must have the same thread pitch. Therefore, in the preferred case of four possible positions spaced by 90°, a four start thread form should be used; and each 90° turn on the member 22 will move it a pre-set axial distance corresponding to one dose for the cartridge 17, on moving the piston 18 the same distance.

The front end 30 of shell 11 includes threads 44 into which connector 12 (which is part of member 21) is permanently screwed via its threads 45. Alternatively, the threads 45 may be omitted, the connector 12 being secured in place by other means, such as an adhesive.

To provide a visual indication of a dose set by winding member 22 away from the stop ring 25, the device includes a cylindrical shell 49 having a number of splines 51. These splines 51 mesh with and rotatably drive splines 52 on a rotating indicator sleeve 53, whilst allowing relative axial movement therebetween. Any suitable number of splines may be provided, and typically 2, 4, 6 or 8 splines may be furnished.

Indicator sleeve 53 surrounds with clearance member 22, and has on its outer surface a helical thread 54 which corresponds to and meshes with thread 44 at the front end 30 of shell 11. These threads have the same lead as the threads of the members 21 and 22, such that one full turn of sleeve 53 gives the same axial movement as one turn of member 22. Carried on the outer surface of the indicator are a multiplicity of numbers such as 0 to 52 in steps of 2 (i.e. 0, 2, 4, 6, etc. up to 52), or 0 to 26 in steps of 1 (i.e. 0, 1, 2, 3 etc. up to 26). Those numbers can be viewed through a window 57 in the shell 11.

Figure 2A:
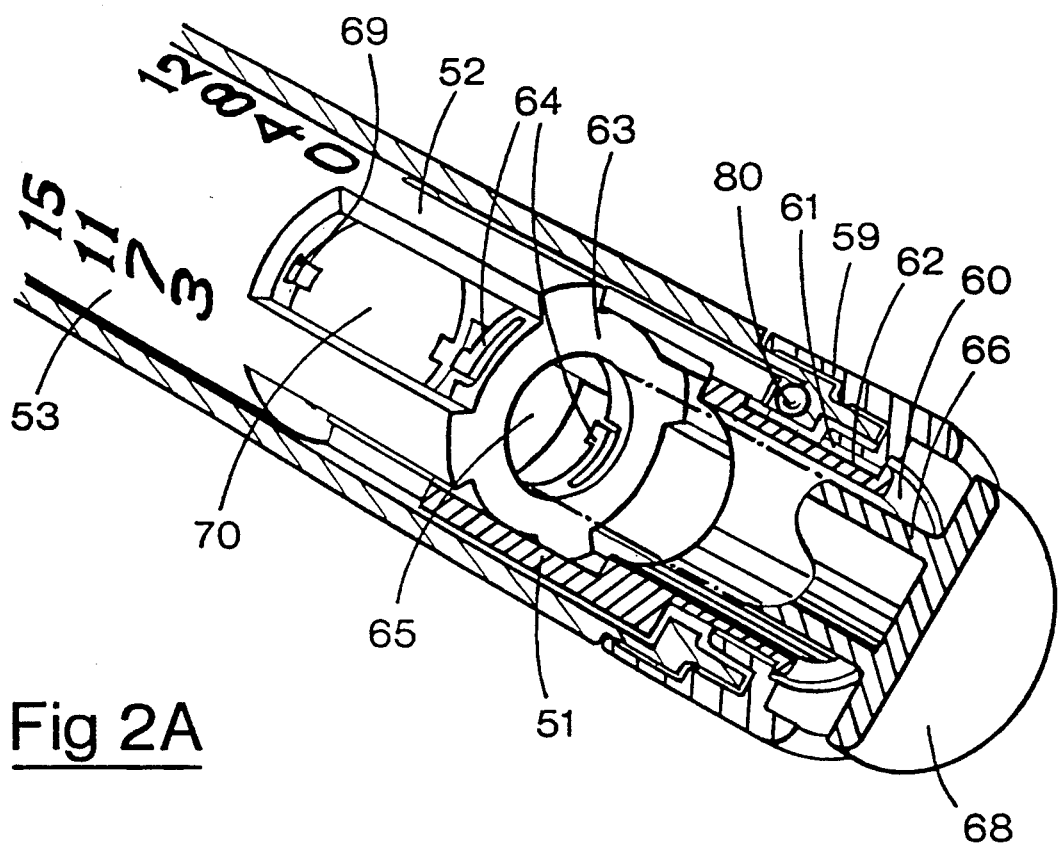
FIG. 2A is a cut-away perspective view from the rear of the device of FIG. 1.
Figure 2B:
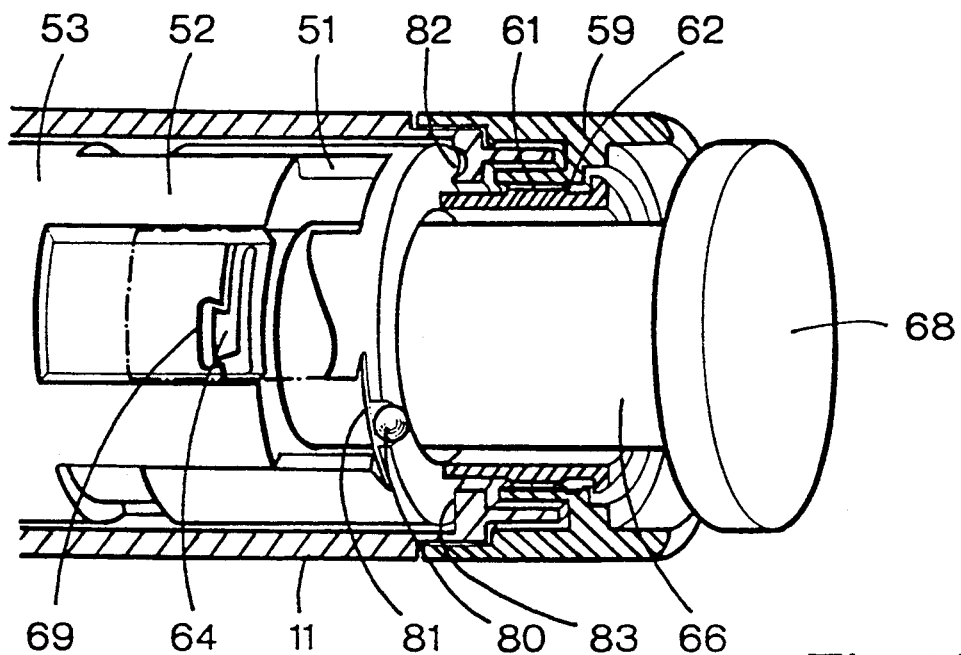
FIG. 2B is a sectional view on the rear of the device.

Indicator sleeve 53 at its end most remote from container 14 is prevented from moving beyond the position at which it indicates the highest reading (say 52 or 26) through window 57 by the bottoming of the splines 51 and 52 in the shell 49 and indicator 53, respectively. Ring 58 is part of shell 49 and acts both as a stop for rearward movement of sleeve 53, and as a mounting for a rotatable end piece 59 which provides a dose setting control knob. End piece 59 is held on shell 49 by a retention lip 60, and splines 61 on end piece 59 engage splines 62 on shell 49 (as shown in FIGS. 2A and 2B), whereby a required dose can be set to appear in window 57 by gripping end piece 59 between finger and thumb and rotating it. The turning movement is transmitted via spines 51 and 52 to indicator sleeve 53, to move the shell 53 on threads 54 and 55 either towards the front end of the device or away from that end, to show various dose numbers through window 57. The extent of forward movement towards the front end (zero reading) is limited by member 22 engaging stop 25.

At its end most remote from container 14, sleeve 53 includes a ring 63 (FIG. 2) on which are formed two or preferably four sprung raised blocks 64, through other numbers of such blocks could be provided. The ring 63 includes a central circular through-aperture 65 which carries stem 66 of a pusher including an outer button 68 for performing actual dose dispensing when pushed to move stem 66 towards the front end of the device 10. The sprung blocks 64 may cooperate with four recesses 69 on the outer face 70 of member 22. There are the same number of recesses 69 on the face 70 as thread starts-namely four, at 90° spacings in the case of a four-start thread, as illustrated.

A ball 80 is positioned in an opening in the end face of the cylindrical shell 49, which ball is urged rearwardly by spring blade 81 and may be partially received in a recess 82 in lip 83 of the outer shell 11. For the described embodiment, four equi-spaced recesses are provided, to give four click-stop positions on each dose-setting turn of end piece 59.

In use, a fresh cartridge 17 containing a fluid to be dispensed (for example, insulin) is placed in container 14, and the container is connected to the device 10 via the threaded connector 12 of member 21. The captive piston 18 is of a sufficiently tight fit in cartridge 17 so that as the container is fitted, the piston bears on the front end 34 of plunger 23 and slides the plunger back in slot 26. Alternatively, plunger 23 may be pushed back by hand. To the front end of the container 14, at the outlet to cartridge 17, there is attached a needle arrangement 71, usually with a safety cap in place (not shown). Also, an additional or alternative safety cap 72 may cover the combination of needle arrangement and container.

For the purpose of dispensing a measured dose the device is set to dose zero by winding end piece 59 clockwise until indicator 53 is wound forward sufficiently to indicate "0" through window 57. In that configuration, blocks 64 engage with recesses 69 of face 70 and button 68 abuts or is closely adjacent end piece 59.

If a dose had fully been dispensed beforehand, member 22 rests on ring 25, whilst sleeve 53 still shows the set dose. The sleeve is wound clockwise by turning end piece 59, which drives the sleeve through splines 51 and 52, advancing the sleeve towards the front. As the blocks 64 protrude by a lesser dimension than the axial motion of member 22 when turned through 90°, re-engagement of the blocks 64 in recesses 69 takes place during the last 90° of movement of sleeve 53 to show "0" through window 57, so re-establishing a connection between member 22 and sleeve 53.

If the dose had not fully been dispensed, turning the end piece 59 will pick up member 22, and thread it forward before the sleeve 53 is reset to "0" by the action of the blocks 64 engaging in recesses 69.

When the member 22 bears on ring 25 and the blocks 64 are engaged in recesses 69, end piece 59 can be turned anti-clockwise to set a new dose to be dispensed.

Dose control knob (end piece 59) is turned anti-clockwise, this motion being transmitted to shell 49 through splines 61. Then, via splines 51 and 52, the dose indicator sleeve 53 is moved helically within the main body shell 11. The pitch on the threads 44 and 54 are the same as the lead on the four-start threads on the members 21 and 22 and plunger 23, and as the sleeve 53 rotates, it moves axially with member 22 and shows successive numbers corresponding to the dose being set by member 22. The numbers are arranged in staggered columns as shown in FIG. 2 so that for each dose indicated the member 22 is set with its threaded segments 29 aligned with channels 28 and spaced from the fixed stop ring 25 by such a distance that corresponding movement of the piston 18 transmitted via the front end 34 of plunger 23 dispenses the indicated dose through the needle 13. Member 22 is then thrust forward by pressing button 68, stem 66 bearing on face 70 of member 22.

Figure 3A:
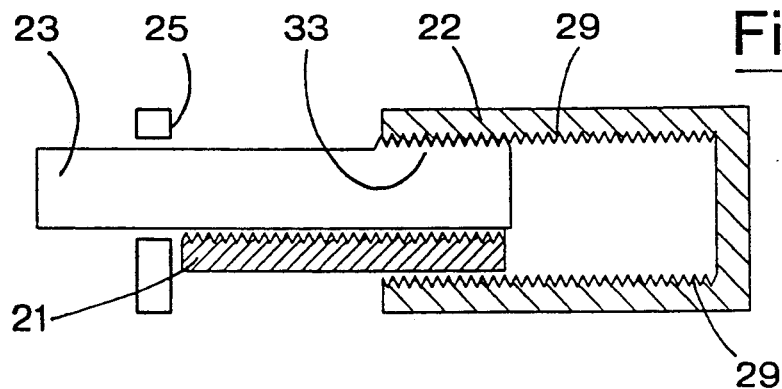
FIGS. 3A and 3B are diagrammatic section views showing the cooperation between first and second threaded members and a plunger, firstly when set for dispensing and secondly after dispensing a dose.
Figure 3B:
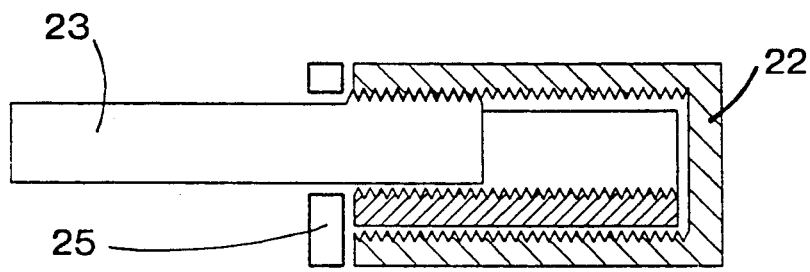
Figure 4A:
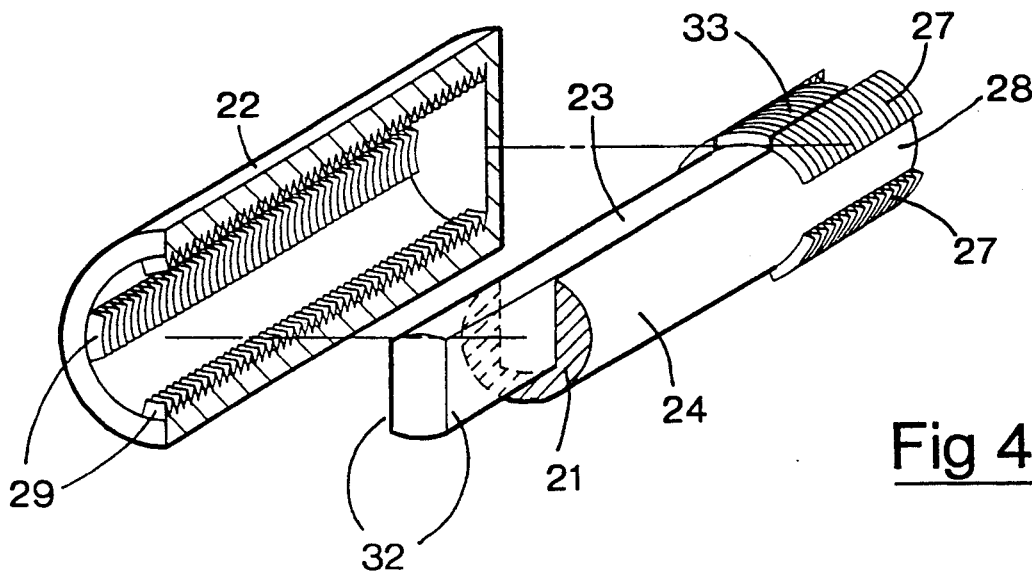
FIGS. 4A and 4B are exploded perspective views respectively of the arrangements of FIGS. 3A and 3B, and of FIGS. 3C and 3D.
Figure 4B:
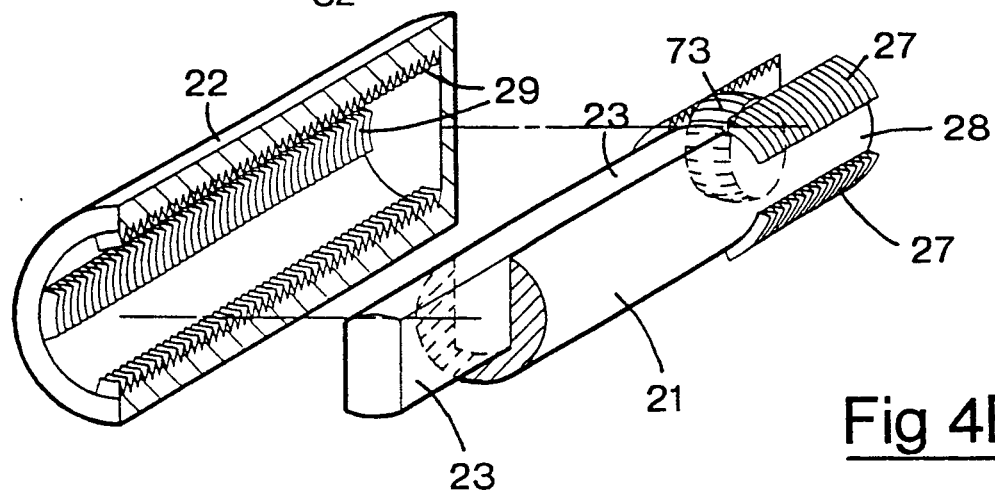

Referring now to FIGS. 3A and 3B, these show the arrangement of the two threaded members 21 and 22 and plunger 23 with threaded segment 33. In FIG. 3A, member 22 is wound back on member 21 and plunger 23 to the position shown. FIG. 3B shows the position of plunger 23 when member 22 is pushed forward by button 68 (not shown). This shows that the forward movement of member 22 gives an equivalent forward movement of plunger 23. The members and plunger are shown in FIG. 4A with member 22 sectioned and displaced from fixed member 21 and plunger 23, for clarity.

Figure 3C:
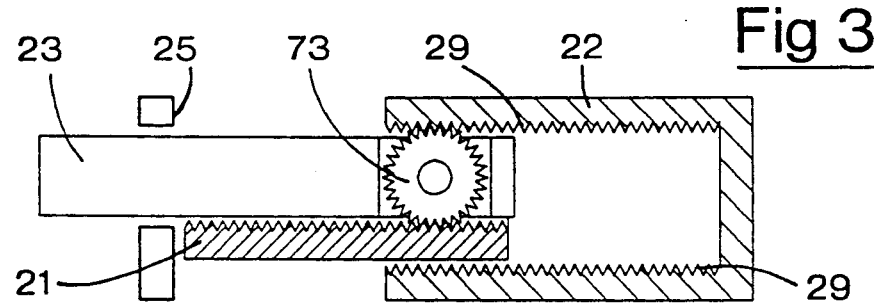
FIGS. 3C and 3D are views similar to those of FIGS. 3A and 3B, but of a second embodiment of plunger having a toothed wheel.
Figure 3D:
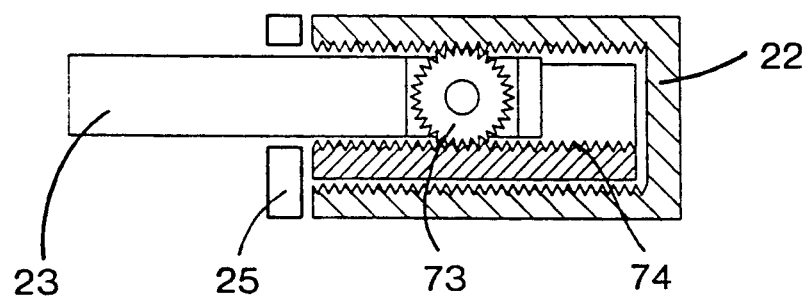

In the alternative arrangement shown in FIG. 3C and 3D, the threaded segment 33 of member 23 is replaced by a toothed wheel 73 having a helically-formed teeth the pitch of which is the same as that of the threads on member 21. In the base of slot 26 of member 21 is a section of thread which is the same pitch form as the threads on members 21 and 22. In FIG. 3C, member 22 is shown wound back on member 21 and wheel 73; in FIG. 3D member 22 is shown pushed forward. Because wheel 73 rolls between the moving thread 29 of member 22 and the fixed thread 74 of member 21, the plunger 23 is moved forward half the distance travelled by member 22. Thus for the same dose setting arrangement as already described above, either half doses may be dispensed for each dose setting or, more importantly, if a larger (usually wider) cartridge is employed, similar doses to those of narrower cartridges can be dispensed by halving the forward movement of the plunger.

Figure 5A:
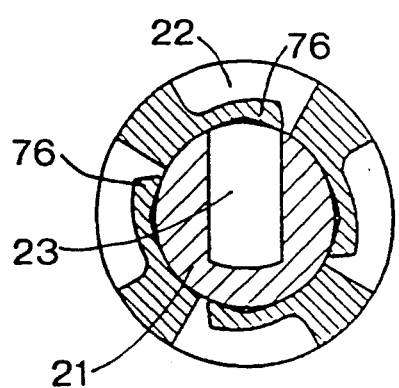
FIGS. 5A and 5B show a lock which limits the rotation of the second threaded member.
Figure 5B:
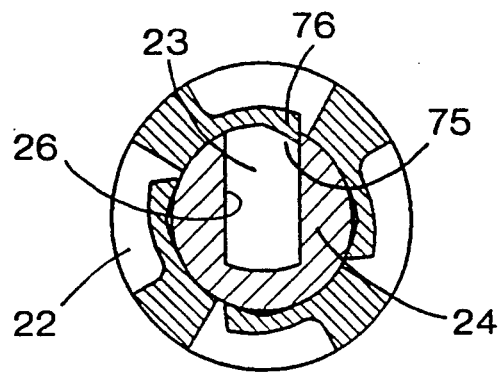

FIGS. 5A and 5B show a stop arrangement for the second member 22, to prevent that member being turned to selected a greater dose than remains for dispensing within the container. The member 22 has four pawls 76 arranged on its front end and which bear on the outer surface of the first member 21 or on the upper surface of the plunger 23, as the member 22 is rotated. The plunger has a recess 75 on its upper surface adjacent its threaded segment 33, into which recess one of the pawls 76 will drop to restrain further rotation of the member 22 in a dose-setting sense when the plunger has been advanced by a pre-determined distance into a container. The splines 61 connecting the end piece 59 to member 22 may be arranged to slip in the event that a pawl 76 locks member 22; once this occurs, member 22 has to be wound back through 45° to release the lock, so that the plunger 23 can be pushed back without also pushing back member 22. Should however member 22 be pushed back as well on replacing cartridge 17, the user need merely wind the member 22 until "0" is showing once more through window 57, to reset the mechanism. It will be appreciated that at the point at which the lock occurs the dose indicator sleeve 53 will show the number of doses remaining in the cartridge.

The embodiments for which an exclusive property or privilege is claimed are defined as follows:

1. A device for dispensing controlled doses of fluid from a container having a piston movable axially in increments thereby to dispense doses of fluid from an outlet of the container, which device comprises a main body having at one end means to connect the device to a container, a plunger mounted for sliding movement within said main body and engageable with the container piston, a fixed stop disposed within the main body adjacent the container connection means and a dose setting and dispensing arrangement disposed within the main body and having first and second threaded members, the first member being fixed in relation to the main body and the second member being mounted for rotation about the first member and having threads engageable with those of the first member, said plunger being mounted within the first member for sliding movement with respect to the main body and having a portion engageable with the threads of the second member, and the second member being rotatable to any one of a plurality of settings where its threads are engaged with said portion of the plunger but free of the first member whereby the second member and plunger may slide axially relative to the first member, movement of the second member in a direction towards the container connection means being limited by said fixed stop, the device further comprising dosage indicator means connected to the second member and arranged to indicate an ascending series of measured doses as the second member is rotated to move along the threads of the first member away from said fixed stop whilst the plunger remains stationary, and for each indicated dose the second member is disposed in one of its said settings relative to the first member where axial movement of the second member is permitted, the second member during such movement driving the plunger to act on the piston of a connected container and the dose expelled thereby being controlled by the axial distance of travel of the second member to the fixed stop from the position to which said member has been turned to indicate a desired dose.

2. A device according to claim 1, configured as the dose dispensing portion of a medical syringe, which device is adapted for connection to the body of the syringe, with the plunger acting on the syringe piston.

3. A device according to claim 1, wherein the first member is threaded externally with a plurality of equispaced threaded arcuate sectors separated by a like plurality of non-threaded sectors, and the second member comprises a hollow cylinder threaded internally with threaded and non-threaded sectors arranged in essentially the same configuration as that of the first member.

4. A device according to claim 3, wherein the first and second members each have four threaded and four non-threaded sectors arranged alternately, and the threads of the threaded sectors of both members are four-start threads.

5. A device according to claim 3, wherein the plunger is slidably received within a slot in the first member, said portion of the plunger projecting through a non-threaded sector of the first member to be engageable with the threads of the second member.

6. A device according to claim 1, wherein said portion of the plunger comprises one of an arcuate threaded portion and a toothed wheel rotatably mounted on the plunger whereby the threads of the second member come into and out of engagement with one of said arcuate threaded portion and toothed wheel upon rotation of said second member.

7. A device according to claim 6 and wherein said portion of the plunger comprises a toothed wheel, there being a toothed rack provided on the main body and with which the toothed wheel meshes, so that the toothed wheel rotates on axial movement of the plunger with respect to said main body.

8. A device according to claim 1, which includes an actuation member mounted on the main body at the end thereof opposed to the container connection means and arranged to move the second member and linked plunger axially towards the fixed stop, the actuation member moving with the second member away from the fixed stop during dose setting.

9. A device according to claim 1, wherein the indicator means comprises a sleeve rotatably mounted on the main body and surrounding the second member, said sleeve carrying a series of dose numbers, and rotation means to rotate both the sleeve and the second member so that the more the second member is threaded away from the fixed stop, the higher will be the indicated dose number.

10. A device according to claim 9, wherein cooperating threads are formed on the sleeve and on the main body whereby the sleeve is moved axially with respect to said main body as the sleeve is rotated.

11. A device according to claim 1, wherein lock means are provided on said main body to restrain rotation of the second member in a sense which moves the second member away from the fixed stop when the plunger projects from the second member by more than a predetermined amount.

12. A device according to claim 8, wherein there is provided a rotatable dose-setting piece and a connector linking the rotatable dose-setting piece to the indicator means, which connector allows relative sliding movement between said rotatable dose-setting piece and said second member whilst holding said rotatable dose-setting piece and said second member against relative rotation.

13. A medication dispenser comprising a body defining a chamber for receiving a container for fluid and having a piston mounted within said container to discharge fluid therefrom, support means at one end of said body for a dispensing needle communicating with an outlet from the container, and a dispensing device according to claim 1, said body of the medication dispenser having at its outer end connection means interengageable with the connection means of said device and said plunger of said device being arranged to contact the piston of a received container.

14. A medication dispensing device comprising:
 (i) a body defining
  a) a chamber for receiving a container for fluid, which container has an outlet and a piston movable axially in increments thereby to dispense doses of fluid through said outlet; and b) support means for a dispensing needle which when supported thereby communicates with said outlet of said container; and (ii) dispensing means provided within said body for dispensing controlled doses of fluid from a received container through a supported needle, which dispensing means comprises:

a) a plunger mounted for sliding movement within said body and engageable with said piston of a received container;

b) a first member disposed within and fixed in relation to said body and threaded externally with a plurality of equi-spaced threaded arcuate sectors separated by a like plurality of non-threaded sectors;

c) a second member mounted for rotation about said first member and having internal threaded and non-threaded sectors arranged in essentially the same configuration as that of the first member, the threaded sectors of the second member being engageable with the threaded sectors of the first member, said plunger being slidably mounted within the first member and having a portion engageable with the threads of the second member, and the second member being rotatable to any one of a plurality of settings where one of the threaded sectors thereof is engaged with said portion of the plunger but all of the threaded sectors of said second member are free of the threaded sector of the first member whereby both the second member and plunger may slide axially relative to the first member;

d) a fixed stop provided on the body adjacent said chamber and arranged to limit sliding movement of the second member in a direction towards a received container; and e) dosage indicator means connected to said second member and arranged to indicate an ascending series of measured doses as the second member is rotated to be screwed along the threads of the first member away from the said fixed stop whilst the plunger remains stationary, the second member being disposed in one of its said settings relative to the first member where axial movement of the second member is permitted for each indicated dose, the second member during such axial movement driving the plunger to act on the piston of a received container and the dose expelled thereby being controlled by the axial distance of travel of the second member to said fixed stop from the position to which said member had been set by rotation, to indicate a desired dose.

* * * * *